(12) United States Patent
Borkovec (10) Patent No.: US 11,051,549 B2
(45) Date of Patent: Jul. 6, 2021

(54) ELECTRONIC SMOKING DEVICE WITH LIQUID RESERVOIR/WICK PORTION

(71) Applicant: Fontem Holdings 1 B.V., Amsterdam (NL)

(72) Inventor: Vaclav Borkovec, Hamburg (DE)

(73) Assignee: Fontem Holdings 1 B.V., Amsterdam (NL)

( * ) Notice: Subject to any disclaimer, the term of this patent is extended or adjusted under 35 U.S.C. 154(b) by 298 days.

(21) Appl. No.: 15/756,491

(22) PCT Filed: Aug. 22, 2016

(86) PCT No.: PCT/EP2016/069770
§ 371 (c)(1),
(2) Date: Feb. 28, 2018

(87) PCT Pub. No.: WO2017/036829
PCT Pub. Date: Mar. 9, 2017

(65) Prior Publication Data
US 2018/0242639 A1     Aug. 30, 2018

(30) Foreign Application Priority Data

Aug. 28, 2015 (EP) .................................... 15183004

(51) Int. Cl.
| | |
|---|---|
| *A24F 13/00* | (2006.01) |
| *A24F 40/42* | (2020.01) |
| *A24F 40/44* | (2020.01) |
| *A24F 40/46* | (2020.01) |
| *A24F 40/10* | (2020.01) |

(Continued)

(52) U.S. Cl.
CPC .............. *A24F 40/42* (2020.01); *A24F 40/44* (2020.01); *A24F 40/46* (2020.01); *A24F 40/10* (2020.01); *A61M 11/044* (2014.02); *A61M 2016/0024* (2013.01)

(58) Field of Classification Search
CPC ..................................................... A24F 47/00
USPC .................................................. 131/328–329
See application file for complete search history.

(56) References Cited

U.S. PATENT DOCUMENTS

| | | |
|---|---|---|
| 2012/0285475 A1 | 11/2012 | Liu |
| 2014/0209105 A1 | 7/2014 | Sears et al. |
| 2014/0270730 A1 | 9/2014 | DePiano et al. |

(Continued)

FOREIGN PATENT DOCUMENTS

| | | |
|---|---|---|
| CN | 203952431 U | 11/2014 |
| EP | 2113178 A1 | 11/2009 |
| EP | 2399636 A1 | 12/2011 |

OTHER PUBLICATIONS

Office Action (Article 94(3) EPC Communication), dated Jan. 30, 2018, in counterpart European patent application No. 15 183 004.9, pp. 1-5.

*Primary Examiner* — Phuong K Dinh
(74) *Attorney, Agent, or Firm* — Dykema Gossett PLLC (57) ABSTRACT

The invention relates to a liquid reservoir/wick portion and to an electronic smoking device comprising a liquid reservoir/wick portion. In order to avoid different liquids undesirably mixing in a wick of the electronic smoking device, the liquid reservoir/wick portion comprises a wick. The wick comprising a liquid receiving side coupled to a liquid storage volume of the liquid reservoir/wick portion, and a liquid supply side coupled to an atomizing element of the electronic smoking device.

17 Claims, 4 Drawing Sheets

(51) Int. Cl.
*A61M 11/04* (2006.01)
*A61M 16/00* (2006.01)

(56) References Cited

U.S. PATENT DOCUMENTS

| | | | |
|---|---|---|---|
| 2015/0196059 A1 | 7/2015 | Liu | |
| 2016/0121058 A1* | 5/2016 | Chen | A24F 40/44 128/200.19 |
| 2016/0143365 A1* | 5/2016 | Liu | A61M 15/06 131/329 |
| 2016/0192710 A1* | 7/2016 | Liu | H05B 3/40 131/329 |
| 2017/0360092 A1* | 12/2017 | Althorpe | F22B 1/284 |

* cited by examiner

ELECTRONIC SMOKING DEVICE WITH LIQUID RESERVOIR/WICK PORTION

FIELD OF INVENTION

The present invention relates generally to electronic smoking devices, in particular electronic cigarettes, and to liquid reservoir/wick portions for electronic smoking devices.

BACKGROUND OF THE INVENTION

An electronic smoking device, such as an electronic cigarette (e-cigarette), typically has a housing accommodating an electric power source (e.g. a single use or rechargeable battery, electrical plug, or other power source), and an electrically operable atomizing element. The atomizing element vaporizes or atomizes liquid supplied from a reservoir and provides vaporized or atomized liquid as an aerosol. Control electronics control the activation of the atomizing element. In some electronic cigarettes, an airflow sensor is provided within the electronic smoking device, which detects a user puffing on the device (e.g., by sensing an under-pressure or an air flow pattern through the device). The airflow sensor indicates or signals the puff to the control electronics to power up the device and generate vapor. In other e-cigarettes, a switch is used to power up the e-cigarette to generate a puff of vapor.

When subsequently using different liquid, these liquids undesirably mix in a wick that supplies the liquid to the atomizer.

SUMMARY OF THE INVENTION

In accordance with one aspect of the present invention, an electronic smoking device is provided, comprising a liquid reservoir/wick portion for providing liquid to be atomized, and an atomizing element for atomizing liquid. The liquid reservoir/wick portion comprises a liquid storage volume and a wick for supplying the liquid from the liquid storage volume to the atomizing element. The wick comprises a liquid receiving side that faces the liquid storage volume. Further, the wick comprises a liquid supply side opposite of the liquid receiving side. The liquid supply side faces away from the liquid storage volume and towards the atomizing element.

In accordance with another aspect of the present invention, a liquid reservoir/wick portion for an electronic smoking device is provided. The liquid reservoir/wick portion comprises a liquid storage volume and a wick. The wick comprises a liquid receiving side that faces the liquid storage volume, and a liquid supply side opposite of the liquid receiving side, the liquid supply side facing away from the liquid storage volume.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Throughout the following, an electronic smoking device, for example an e-cigarette, will be exemplarily described with reference to the drawings.

Figure 1:
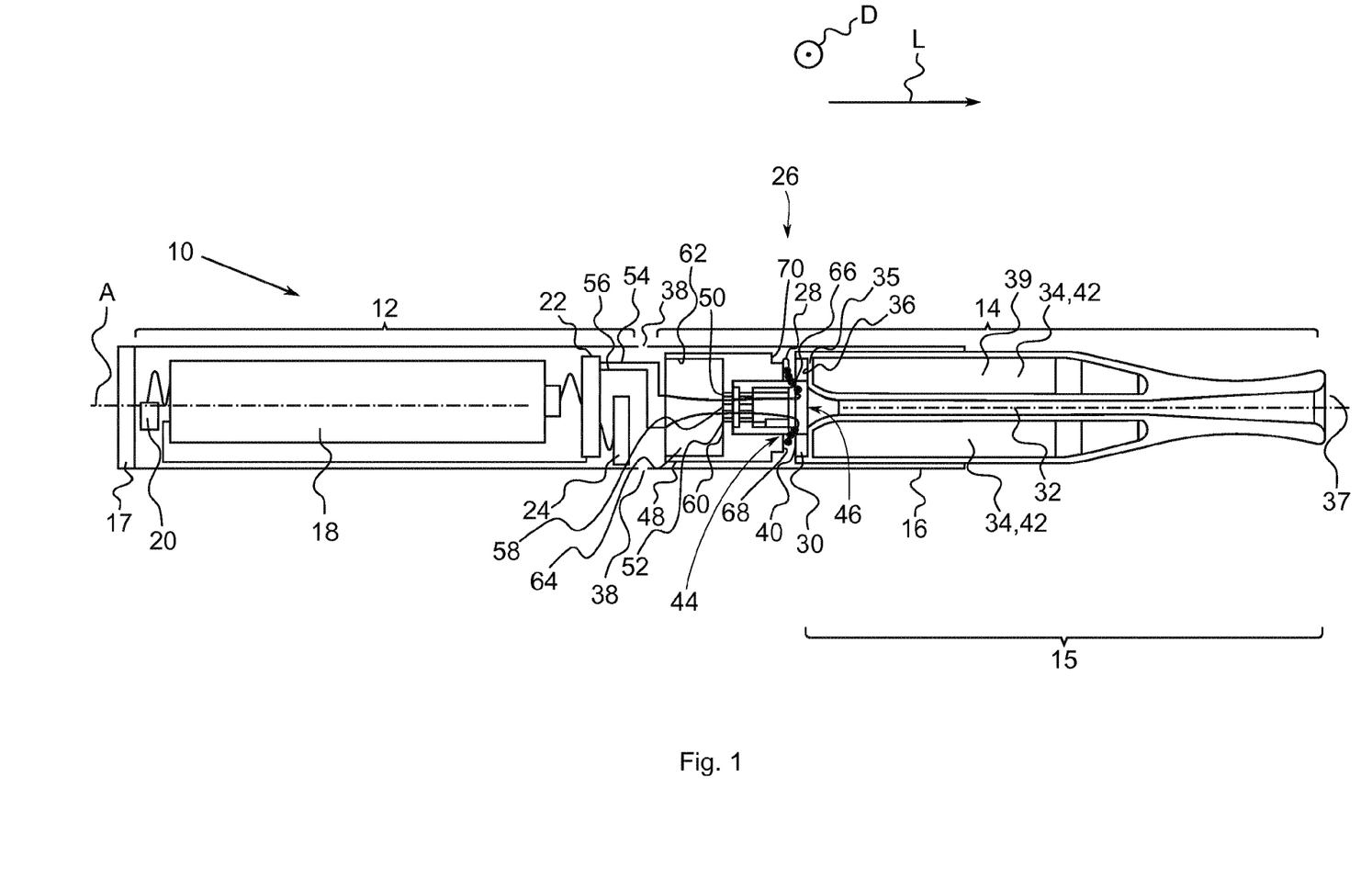
FIG. 1 is a schematic cross-sectional illustration of an exemplary embodiment of an electronic smoking device.

As is shown in FIG. 1, an electronic smoking device 10 typically has an outer housing 16 comprising a cylindrical hollow tube and an end cap 17. The outer housing 16 may comprise a single-piece or a multiple-piece tube. In FIG. 1, the outer housing 16 is shown with a two-piece structure having a battery portion 12 and an atomizer/liquid reservoir portion 14. The atomizer/liquid reservoir portion 14 is shown with a liquid reservoir/wick portion 15 that may be an integral part of the atomizer/liquid reservoir portion 15 or a separate part that is exchangeably fixed to the rest of the electronic smoking device 10 and for example to the battery portion 12.

Together, the battery portion 12 and the atomizer/liquid reservoir portion 14 form the outer housing 16, e.g. the cylindrical tube, which can be approximately the same size and shape as a conventional cigarette, typically about 100 mm with a 7.5 mm diameter, although lengths may range from 70 to 150 or 180 mm, and diameters from 5 to 20 mm.

The outer housing 16 is typically made of metal, e.g. steel or aluminum, or of hardwearing plastic, and may comprise the end cap 17 to provide a closed housing to contain the components of the electronic smoking device 10. The battery portion 12 and an atomizer/liquid reservoir portion 14 or the liquid reservoir/wick portion 15 may be configured to fit together by a friction push fit, a snap fit, or a bayonet attachment, magnetic fit, or screw threads. The end cap 17 is provided at the front end of the battery portion 12. The end cap 17 may be made from translucent plastic or other translucent material to allow a light-emitting diode (LED) 20 positioned near the end cap to emit light through the end cap. The end cap can be made of metal or other materials that do not allow light to pass.

An air inlet may be provided in the end cap 17, at the edge of the end cap 17 next to the cylindrical hollow tube, anywhere along the length of the cylindrical hollow tube, or at the connection of the battery portion 12 and the atomizer/liquid reservoir portion 14. FIG. 1 shows a pair of air inlets 38 provided at the intersection between the battery portion 12 and the atomizer/liquid reservoir portion 14.

A battery 18, the LED 20, control electronics 22 and optionally an airflow sensor 24 are provided within the outer housing section of the battery portion 12. The battery 18 is electrically connected to the control electronics 22, which are electrically connected to the LED 20 and the airflow sensor 24. In this example the LED 20 is at the front end of the battery portion 12 adjacent to the end cap 17, and the control electronics 22 and the airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the electronic smoking device 10. The airflow sensor 24 can be any suitable sensor for detecting changes in airflow or air pressure, such as a microphone switch including a deformable membrane, which is caused to move by variations in air pressure. Alternatively the sensor may be a Hall element or an electro-mechanical sensor.

The control electronics 22 are also be connected to an atomizing element 26. In the example shown, the atomizing element 26 includes a heating coil 28, which is pressed against a wick 30 extending around a central passage 32 of the atomizer/liquid reservoir portion 14. The atomizing element 26 may alternatively comprise other types of heating elements, such as ceramic heaters, or fiber or mesh material heaters. Nonresistance atomizing elements such as sonic, piezo and jet spray may also be used in the atomizer in place of the heating coil.

The central passage 32 is surrounded by a cylindrical liquid reservoir 34 with a liquid receiving side 35 of the wick 30 facing or even abutting on a front face 36 of the liquid reservoir 34. The wick 30 may be a porous material such as a bundle of fiberglass fibers or comprise or even consist of silicon dioxide, with liquid in the liquid reservoir 34 drawn by capillary action from the liquid receiving side 32 towards the atomizing element 26.

The liquid reservoir 34 may alternatively include wadding soaked in liquid which encircles the central passage 32 with the wick 30 abutting the wadding. In other embodiments the liquid reservoir 34 may comprise a toroidal cavity arranged to be filled with liquid and with the wick 30 extending into the toroidal cavity.

An air inhalation port 37 is provided at the back end of the atomizer/liquid reservoir portion 14, e.g. of the liquid reservoir/wick portion 15, remote from the end cap 17. The air inhalation port 37 may be formed from the cylindrical hollow tube of the atomizer/liquid reservoir portion 14 or may be formed by the liquid reservoir/wick portion 15.

In use, a user sucks on the electronic smoking device 10. This causes air to be drawn into the electronic smoking device 10 via one or more air inlets, such as air inlets 38, and to be drawn through the central passage 32 towards the air inhalation port 37. The change in air pressure, which arises is detected by the airflow sensor 24, which generates an electrical signal that is passed to the control electronics 22. In response to the signal, the control electronics 22 activate the atomizing element 26, which causes liquid present in the wick 30 to be vaporized creating an aerosol (which may comprise gaseous and liquid components) within the central passage 32. As the user continues to suck on the electronic smoking device 10, this aerosol is drawn through the central passage 32 and inhaled by the user. At the same time the control electronics 22 also activate the LED 20 causing the LED 20 to light up which is visible via the translucent end cap 17 mimicking the appearance of a glowing ember at the end of a conventional cigarette. As liquid present in the wick 30 is converted into an aerosol more liquid is drawn into the wick 30 from the liquid reservoir 34 by capillary action and thus is available to be converted into an aerosol through subsequent activation of the atomizing element 26.

Some electronic smoking devices are intended to be disposable and the electric power in the battery 18 is intended to be sufficient to vaporize the liquid contained within the liquid reservoir 34, after which the electronic smoking device 10 is thrown away. In other embodiments the battery 18 is replaceable or rechargeable and the liquid reservoir 34 is replaceable or refillable. In the cases where the liquid reservoir 34 comprises a toroidal cavity as liquid storage volume, this may be achieved by refilling the liquid reservoir 34 via a refill port. In other embodiments the atomizer/liquid reservoir portion 14 of the electronic smoking device 10 is detachable from the battery portion 12 and another atomizer/liquid reservoir portion 14 can be fitted with another liquid reservoir 34 thereby replenishing the supply of liquid. In some cases, replacing the liquid reservoir 34 may involve replacement of the atomizing element 26 and the wick 30 along with the replacement of the liquid reservoir 34. A replaceable unit comprising the atomizing element 26 and the liquid reservoir 34 is called a cartomizer. Alternatively, the liquid reservoir/wick portion 15 can be exchanged for another liquid reservoir/wick portion 15, wherein the atomizing element 26 is detachably connected or connectable to the liquid reservoir/wick portion 15 and in particular to the wick 30.

The other liquid reservoir 34 may be in the form of a cartridge having a central passage 32 through which a user inhales aerosol. In other embodiments, aerosol may flow around the exterior of the cartridge 32 to the air inhalation port 36, or via dedicated channels embedded in sidewalls of the cartridge 32.

Of course, in addition to the above description of the structure and function of a typical electronic smoking device 10, variations also exist. For example, the LED 20 may be omitted. The airflow sensor 24 may be placed adjacent the end cap 17 rather than in the middle of the electronic smoking device. The airflow sensor 24 may be replaced with a switch which enables a user to activate the electronic smoking device manually rather than in response to the detection of a change in air flow or air pressure.

Opposite of the liquid receiving side 35, the wick 30 is formed with a liquid supply side 40 that faces away from the liquid reservoir 34 and in particular from its liquid storage volume 42. The liquid supply side 40 faces towards the atomizing element 26 and even contacts the atomizing element 26 in case the liquid reservoir/wick portion 15 is part of the electronic smoking device 10. The atomizing element 26 according to the exemplary embodiment of FIG. 1 is pressed against the wick 30 in a longitudinal direction L, along which the central passage 32 extends towards the air inhalation port 37. Hence, the wick 30 is at least partly arranged between the atomizing element 26 and the liquid reservoir 34, in particular the liquid storage volume 42 of the liquid reservoir 34.

The central passage 32 is surrounded by the liquid storage volume 42 and may extend through the liquid storage volume 42 along the longitudinal direction L. The liquid storage volume 42 may have the shape of a torus.

The liquid reservoir/wick portion 15 comprises a wick receiving opening 44, in which the wick 30 is at least partly or even completely arranged. The wick receiving opening 44 opens against the longitudinal direction L, i.e. away from the air inhalation port 37 and/or towards the atomizing element 26. The central passage 32 opens into the wick receiving opening 44 against the longitudinal direction L.

Through the wick 30, a flow-through opening 46 extends, via which air can flow into the central passage 32 and towards the air inhalation port 37. The flow through opening 46 extends along the longitudinal direction L through the wick 30 and/or at least partly through the atomizing element 26. The flow-through opening 46 may be arranged centrally in the wick 30 and may, thus, be designated as central opening of the wick 30.

The electronic smoking device 10 comprises a press part 48 that presses the atomizing element 26 against the liquid supply side 40 of the wick 30. Thus, in the longitudinal direction L, the press part 48 is arranged before the atomizing element 26. The atomizing element 26 is arranged between the press part 48 and the liquid reservoir/wick portion 15, in particular its wick 30.

The press part 48 is provided with at least two through holes 50, 52, via which the atomizing element 26 is connected to the control electronics 22 by wires 54, 56. The wires 54, 56 may extend through one of the through holes 50, 52, or may each extend through one of the through holes 50, 52. In case both wires 54, 56 together extend through one of the through holes 50, 52, another one of the through holes 50, 52 may be used for letting air flow into the central passage 32. In case each of the wires 54, 56 is arranged in a different one of the through holes 50, 52, the press part 48 comprises a separate through hole 58, via which air is led into the central passage 32. The through hole that lets air pass into the central passage 32 when a user sucks on the air inhalation port 37 is free of any wire 54, 56.

The through holes 50, 52, 58 extend through a holding wall 60 with a predetermined thickness parallel to the longitudinal direction L. The through holes 50, 52 in the holding wall 60 position the wires 54, 56 such that the wires 54, 56 do not unduly hinder air from flowing into the central passage 32. However, in order to minimize the flow resistance of the through hole via which air passes mainly into the central passage 32, the thickness of the holding wall 60 and the resulting length of this through hole along the longitudinal direction L has to be minimized. Yet, the press part 48 needs to have a certain predefined length along the longitudinal direction L in order to be stably positioned inside of the outer housing 60 and to have a mechanical strength sufficient for pressing the atomizing element 26 against the wick 30. Therefore, the press part 48 is formed with a guiding wall 62 that extends away from the atomizing element 26 and against the longitudinal direction L. The guiding wall 62 completely extends around a central axis A of the electronic smoking device 10 in a circumferential direction D of the electronic smoking device 10, the circumferential direction D extending perpendicular to the longitudinal direction L. The central axis A extends parallel to the longitudinal direction L. For example, the central passage 32 extends along the central axis A, wherein the central axis A may be a central axis A of the liquid reservoir 34 and in particular of its central passage 32.

The guiding wall 62 prevents that the press part 48 tilts and probably even jams when the press part 48 is introduced into the outer housing 60.

The guiding wall 62 protrudes from the holding wall 60 against the longitudinal direction L and encircles a free volume 64 in the circumferential direction D. The free volume 64 opens against the longitudinal direction L and away from the atomizing element 26. The free volume 64 interconnects the through hole, through which air is supplied to the central passage 32, and the air inlets 38, wherein an inner diameter of the free volume 64 perpendicular to the central axis A is larger than the corresponding inner diameter of the through hole guiding the air or of all through holes 50, 52, 58 combined.

The press part 48 comprises a press-in collar 66, whose outer diameter perpendicular to the central axis A corresponds to or is smaller than the inner diameter of the flow through opening 46 of the wick 30. The press-in collar 66 protrudes from a pressing surface 68 that presses the atomizing element 26 at least partly against the liquid supply side 40 of the wick 30. The press-in collar 66 may at least section-wise be introduced into the flow through opening 46. Furthermore, it may press at least a part of the atomizing element 26 into the flow through opening 46. In case the wick 30 comprises or consists of a heating coil made of a wound heating wire, at least one winding of the heating coil may be pressed into the flow through opening 48 by the press-in collar 66.

The press part 48 is shown with a recess 70 that extends around the central axis A in the circumferential direction D. The recess 70 opens away from the central axis A and in the longitudinal direction L, i.e. towards the liquid reservoir/wick portion 15. An outer diameter of the recessed section of the press part 48 corresponds to or is smaller than the inner diameter of the wick receiving opening 44, such that the recessed section can at least partly be introduced into the wick receiving opening 44, thereby pressing the atomizing element 26 further into the wick 30 in order to increase the contact surface between the atomizing element 26 and the wick 30.

The liquid reservoir/wick portion 15 may be configured to be replaceable, i.e. to be repeatedly mountable and removable and/or to be exchangeable for another liquid reservoir/wick portion 15. For example, the liquid reservoir/wick portion 15 can be detachably connected to the atomizing element 30.

Figure 2:
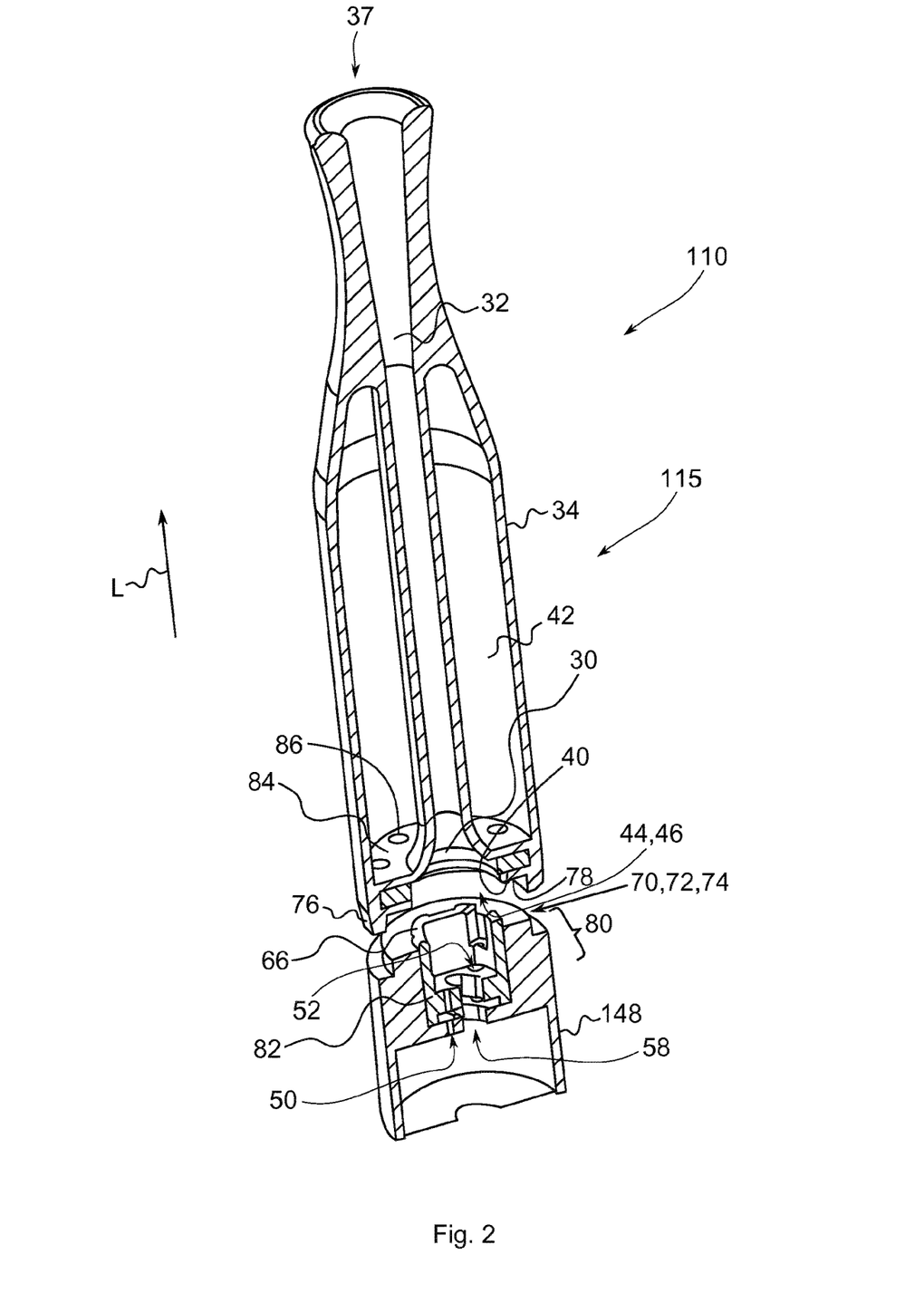
FIG. 2 is a schematic cross-sectional view of parts of another exemplary embodiment of the electronic smoking device.

FIG. 2 shows another exemplary embodiment of the electronic smoking device, wherein only the liquid reservoir/wick portion and the press part are shown in a schematic cross-sectional view. The atomizing element 26 is omitted in FIG. 2 for the sake of simplicity.

The electronic smoking device 110 comprises a liquid reservoir/wick portion 115 and a press part 148. The recessed section 72 comprises a fixing section for affixing the press part 148 to the liquid reservoir/wick portion 115. The liquid reservoir/wick portion 115 comprises a counter fixing portion 76 for the fixing portion 74 of the press part 148. Via the fixing portion 74 and the counter fixing portion 76, the liquid reservoir/wick portion 115 can be captively fixed to the press part 148. For example, the fixing portion 74 and the counter fixing portion 76 may be configured to affix the liquid reservoir/wick portion 115 to the press part 148 by a friction-push fit, a snap fit, a bayonet attachment, a magnetic fit or a screw fit. Hence, the fixing portion 74 may comprise an outer thread and the counter fixing portion 76 may comprise an inner thread for the outer thread.

Against the longitudinal direction L and opposite of the air inhalation port 37, a sealing foil 78 is arranged on the liquid supply side 40 of the wick 30 in order to prevent that liquid stored in the liquid reservoir 34 can inadvertently flow out of the wick 30. When connecting the liquid reservoir/wick portion 115 to the press part 148, for example when assembling the electronic smoking device 110 during production or by a consumer, this sealing foil 78 needs to be removed prior to assembly.

In the following, features of the electronic smoking device 110, which the electronic smoking device 10 of the previous exemplary embodiment may also comprise, are described.

As clearly visible in the schematic cross-sectional perspective view of FIG. 2, an inner diameter perpendicular to the longitudinal direction L of the through hole 58 for the air is larger than corresponding inner diameters of the through holes 50, 52 for the wires 54, 56.

The press-in collar 66 is formed as an open end of a sleeve section 80 of an insert 82 inserted into the press part 148. The sleeve section 80 provides for the press-in collar 66 and comprises an inner free volume for the wires 54, 56 and the air passing towards the central passage 32. Hence, again, flow resistance for the air is not unduly increased due to the free volume of the sleeve section 80.

In the longitudinal direction L, the wick receiving opening 44 comprises a base 84 that is arranged between the wick 40 and the liquid storage volume 42. The central passage 32 extends through the base 84 in the longitudinal direction L and towards the air inhalation port 37. Hence, the base 84 and/or the wick may be described as being ring-shaped.

The base 84 comprises at least one and for example several liquid conduits 86 that interconnect the liquid storage volume 42 and the wick 30 in a liquid-conducting manner. For example, the liquid conduits 86 extend through the base 84 parallel to the longitudinal direction L. The wick 30 is attached to the base 84 of the liquid storage volume 42, the base 84 being provided with liquid conduits 86 in order to supply liquid to the wick 30 through the liquid conduits 86.

For example, the liquid receiving side 35 of the wick 30 is in contact with the front face 36 of the liquid reservoir 34, the front face 36 facing the atomizing element 26 and/or away from the liquid storage volume 42 and being permeable for liquid. The front face 36 is for example a face of the base 84 of the liquid storage volume 42 that can face the longitudinal direction L of the electronic smoking device 10 and for example of the liquid reservoirs/wick portion 15.

The base 84 of the liquid storage volume 42 is shown with the at least one and for example several liquid conduits 86 that interconnect the liquid storage volume 42 and the wick 30 in a liquid-conducting manner. For example, the liquid conduits 86 extend through the base 84 parallel to the longitudinal direction L of the electronic smoking device 10, 110 and for example of the liquid reservoirs/wick portion 15, 115. The wick 30 can be attached to the base 84 of the liquid storage volume 42. The base 30 is provided with the liquid conduits 86 in order to supply liquid to the wick 30 through the liquid conduits 86.

Figure 3:
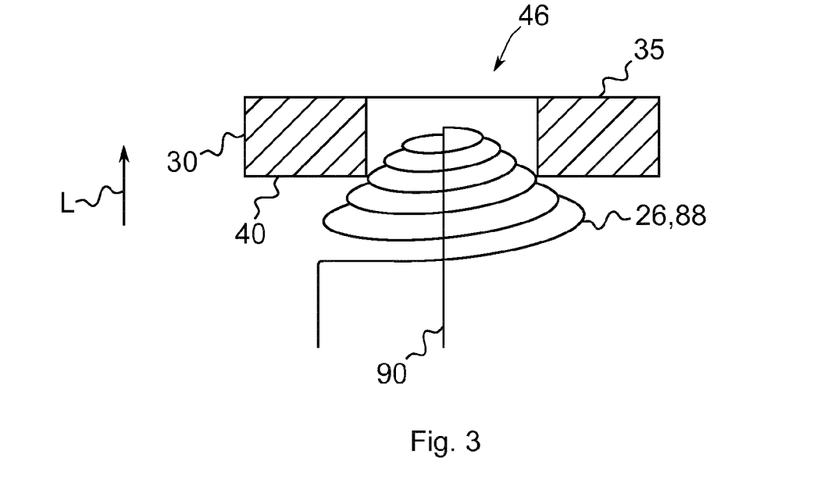
FIGS. 3 to 6 are schematic views of exemplary embodiments of atomizing elements and wicks according to the invention.
Figure 4:
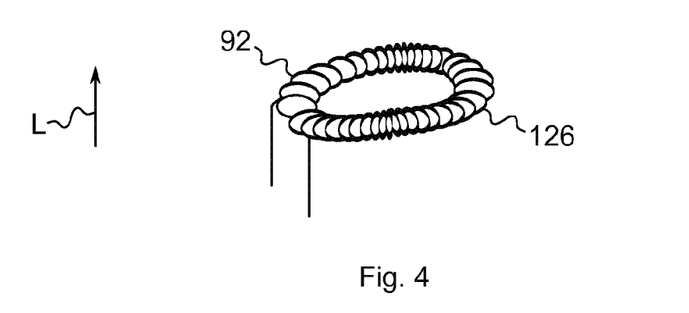
Figure 5:
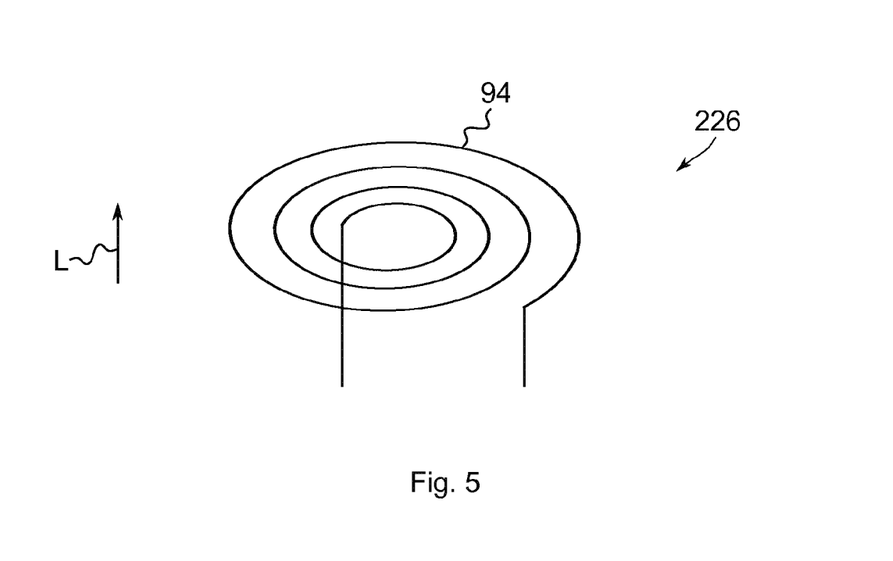

FIGS. 3 to 5 show different embodiments of atomizing elements 26 in schematic perspective views.

FIG. 3 shows the atomizing element 26 of the previous embodiments in a state in which the atomizing element 26 is not pressed against the wick 30 and, thus, in a not deformed state. For the sake of clarity, the wick 30 is shown in a cross-sectional side view with the cross-sectional plane extending through the central axis A.

An envelope or outer form of the atomizing element 26 is essentially cone-shaped, wherein a wider base of the atomizing element 26 is arranged before the wick 30 in the longitudinal direction L, and a narrower tip of the atomizing element 26 is shown arranged inside of the flow through opening 46 of the wick 30.

The atomizing element 26 is shown as a heating coil with a plurality of windings 88 with a diameter that decreases in the longitudinal direction. In particular, the windings 88 are wound around an inner wire section 90.

FIG. 4 shows another exemplary embodiment of the atomizing element than can be combined with the ring-shaped wick 30.

The atomizing element 126 of FIG. 4 is formed by a heating wire that forms a plurality of windings 92 with a constant diameter. A winding axis of the atomizing element 26, around which the windings 92 are wound, is ring-shaped, such that the windings 92 and, hence, the atomizing element 126, is torus-shaped.

FIG. 5 shows another exemplary embodiment of the atomizing element. The atomizing element 226 of FIG. 5 is formed by a heating wire that is wound to a plurality of windings 94 with an increasing diameter. However, all windings 94 of the atomizing element 226 are arranged in a common plane.

Figure 6:
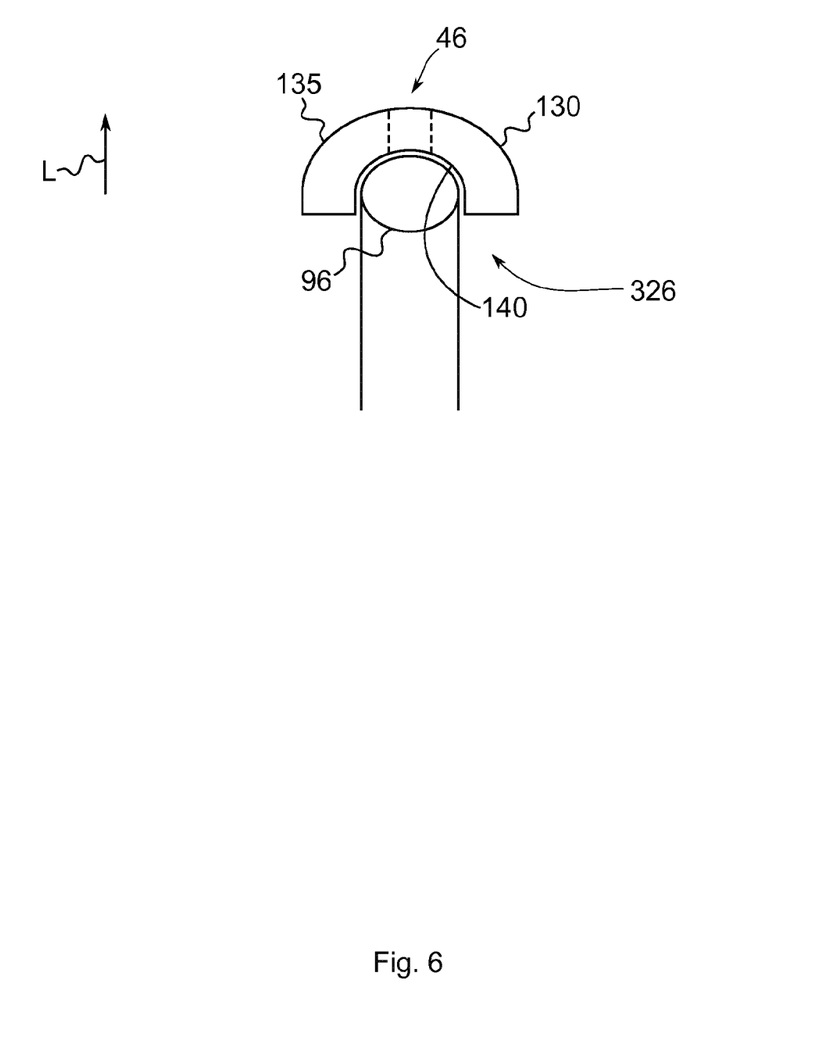

FIG. 6 shows another exemplary embodiment of the atomizing element 326 and of the wick.

The atomizing element 326 is formed by a heating wire with a plurality of windings 96, which are wound around a straight winding axis and which have a constant diameter. Hence, the windings 96 form the atomizing element 326 with a hollow cylindrical shape.

At least the liquid supply side 140 of the wick 130 has an arced shape and encompasses the atomizing element 326 at least section-wise. For example, the wick 130 forms a channel, into which the windings 96 of the atomizing element 326 can at least partly and for example half-way be introduced. Introducing the windings 96 half-way can mean that the windings 96 can all be introduced into the channel until a depth that corresponds to half of the winding diameter of the windings 96.

The flow through opening 46 extends along the longitudinal direction L through the wick 130. For example, not only the liquid supply side 140 but also the liquid receiving side 135 have an arc shape and extend parallel to each other, wherein the flow through opening 46 is arranged at a center of the wick 130 perpendicular to the longitudinal direction L.

In summary, in one aspect, the electronic smoking device comprises a liquid reservoirs/wick portion for providing liquid to be atomized, and an atomizing element for atomizing liquid, wherein the liquid reservoir/wick portion comprises a liquid storage volume and a wick for supplying the liquid from the liquid storage volume to the atomizing, wherein the wick comprises a liquid receiving side that faces the liquid storage volume, and a liquid supply side opposite the liquid receiving side, the liquid supply side facing away from the liquid storage volume and towards the atomizing element. In another aspect, a liquid reservoir/wick portion for an electronic smoking device is provided, the liquid reservoir/wick portion comprising a liquid storage volume and a wick, wherein the wick comprises a liquid receiving side that faces the liquid storage volume, and a liquid supply side opposite of the liquid receiving side, the liquid supply side facing away from the liquid storage volume.

An advantage of the electronic smoking device according to the one aspect and the liquid reservoir/wick portion according to the other aspect may be that the wick can be replaced more easily by another wick, for example in case another and for example a different liquid shall be atomized with the electronic smoking device, without mixing the two liquids in one wick.

According to an embodiment, the wick has a central opening that is in communication with a central passage of the liquid reservoir, the central passage extending away from the atomizing element and towards an air inhalation port of the electronic smoking device. An advantage of such an embodiment may be that atomized liquid can easily and with low flow resistance enter the central passage through the wick. As the central opening facilitates that atomized liquid can flow into the central passage, the central opening may also be designated as flow through opening. In case the liquid reservoir/wick portion is provided separate from other elements of the electronic smoking device, the central passage may extend through the central opening of the wick in a state in that the liquid reservoir/wick portion is mounted to the electronic smoking device. The liquid reservoir/wick portion may be configured to be replaceable, i.e. to be repeatedly mountable and removable and/or to be exchangeable for another liquid reservoir/wick portion. For example, the liquid reservoir/wick portion can be detachably connected to the atomizing element.

According to an embodiment, the liquid receiving side may be in contact with a front face of the liquid reservoir, the front face facing the atomizing element and/or away from the liquid storage volume, and being permeable for liquid. The front face may be a face of a base of the liquid storage volume that can face a longitudinal direction of the electronic smoking device and for example of the liquid reservoirs/wick portion. In case the liquid reservoir/wick portion is provided separate of other elements of the electronic smoking device, e.g. in case the liquid reservoir/wick portion is not mounted, the front face may face away from the air inhalation port of the liquid reservoir/wick portion. An advantage of this embodiment may be that liquid can readily flow through the permeable front face into the wick, wherein a total contact surface between the wick and the front face is merely limited by the outer diameter of the wick and the diameter of its central opening and can, therefore, be comparably large.

The base of the liquid storage volume may comprise at least one and for example several liquid conduits that interconnect the liquid storage volume and the wick in a liquid-conducting manner. For example, the liquid conduits extend through the base parallel to the longitudinal direction of the electronic smoking device and for example of the liquid reservoirs/wick portion. The wick may be attached to the base of the liquid storage volume. The base may be provided with the liquid conduits in order to supply liquid to the wick through the liquid conduits.

According to an embodiment, the front face may encircle the central passage. An advantage of this embodiment may be that the total contact surface between the front face and the wick is maximized. Another advantage of this embodiment may be that the wick can be rotationally symmetrically supplied with liquid to be atomized with respect to a central access of the central passage.

According to an embodiment, the atomizing element may be in contact with the liquid supply side. An advantage of this embodiment may be that due to the direct contact between the atomizing element and the liquid supply side, liquid is brought into direct contact with the atomizing element by the wick, thereby facilitating atomization of the liquid.

According to an embodiment, the wick may have a hollow cylindrical shape and for example an annular or ring shape. An advantage of such embodiments may be that the wick can be easily produced with a flow through opening that may be formed as the central opening, and a shape adapted to the shape of the front face, for example by punching.

According to an embodiment, the liquid supply side has an arced shape and encompasses the atomizing element at least section wise. An advantage of such an embodiment may be that a contact surface between the atomizing element and the wick can be maximized while minimizing a total size of the wick/atomizing element combination, in particular a width perpendicular to the central axis. Hence the electronic smoking device or at least the liquid reservoir/wick portion can have a sleek appearance. In case the liquid reservoir/wick portion is provided separate from other elements of the electronic smoking device, the liquid supply side may form an opening and for example a channel that opens a way from the air inhalation port. The central passage can be arranged opposite of the open side of the opening for channel in a base of the opening or channel.

According to an embodiment, an envelope, i.e. an outer shape or silhouette, of the atomizing element may be essentially cone-shaped. A sleeker tip of the cone-shaped atomizing element may at least sectionwise be introduced or introducible into the central opening. A broader base of the cone-shaped atomizing element may have a diameter perpendicular to the central axis that is larger than the diameter of the central opening and that may be smaller than an outer diameter of the wick. An advantage of such an embodiment may be that the wick can be easily positioned with respect to the atomizing element when the liquid reservoir/wick portion is added to and e.g. assembled with other components of the electronic smoking device in order to form the electronic smoking device. In particular the sleeker tip of the cone-shaped atomizing element may be used for guiding the atomizing element and/or the wick when combining the liquid reservoir/wick portion with the atomizing element.

The cone-shaped atomizing element may be a heating coil with an inner wire section, around which windings with an increasing diameter are wound from the tip of the cone-shaped atomizing element and along the inner wire section. An advantage of such an embodiment may be that the cone-shaped atomizing element can be easily produced by winding a heating wire.

According to another embodiment, the atomizing element may be a heating coil, whose windings have a constant diameter. An advantage of such an embodiment may be that the atomizing element can be formed even more easily. Another advantage may be that such an atomizing element may have a hollow cylindrical shape, which facilitates combining the atomizing element and the wick, in particular in case the liquid supply side of the wick has an arced shape and forms a groove for receiving the atomizing element.

According to another embodiment, the atomizing element may be torus-shaped and for example a torus-shaped heating coil. Inner and outer diameters of the torus-shaped atomizing element may essentially correspond to inner and outer diameters of the wick with the central opening, such that a total contact surface between the atomizing element and the wick can be maximize.

According to another embodiment, the atomizing element comprises a spirally formed heating wire. The spirally formed heating wire may extend in a plain parallel to the wick and for example perpendicular to the central access or the central passage. Hence, the atomizing element can be easily placed against the liquid supply side of the wick with a large contact surface. Perpendicular to the central axis, the spirals formed by the heating wire may be wound at a distance to each other. An advantage of such an embodiment may be that the atomizing element can be easily formed, providing a large contact surface between the atomizing element and the wick, wherein air can easily flow through the atomizing element and the central opening into the central passage and towards the air inhalation port.

Components in contact with the atomizing element, for example the wick or a press part that may press the atomizing element against the wick, may be formed of a ceramic, for example silicone dioxide. An advantage of such an embodiment may be that heat produced by the atomizing element does not affect other components of the electronic smoking device, in particular of the liquid reservoir/wick portion.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS

10, 110 electronic smoking device
12 battery portion 14 atomizer/liquid reservoir portion
15, 115 liquid reservoir/wick portion
16 outer housing
17 end cap
18 battery
20 light-emitting diode (LED)
22 control electronics
24 airflow sensor
26, 126, 226, 326 atomizing element
28 heating coil
30, 130 wick
32 central passage
34 liquid reservoir
35, 135 liquid receiving side
36 front face
37 air inhalation port
38 air inlets
40, 140 liquid supply side
42 liquid storage volume
44 wick receiving opening
46 flow through opening/central opening
48, 148 press part
50, 52, 58 through hole
54, 56 wire
60 holding wall
62 guiding wall
64 free volume
66 press-in collar
68 pressing surface
70 recess
72 recessed section
74 fixing portion
76 counter fixing portion
78 sealing foil
80 sleeve section
82 insert
84 base
86 liquid conduit
88 winding
90 inner wire section
92 winding
94 winding
96 winding
A central axis
D circumferential direction
L longitudinal direction

The invention claimed is:

1. An electronic smoking device comprising:
a liquid reservoir/wick portion including a liquid storage volume and a wick configured and arranged for supplying the liquid from the liquid storage volume to an atomizing element when the liquid reservoir/wick portion is coupled to the atomizing element; and
the atomizing element configured and arranged for atomizing liquid;
wherein the wick includes a liquid receiving side coupled to the liquid storage volume, and a liquid supply side coupled to the atomizing element when the liquid reservoir/wick portion is coupled to the atomizing element;
wherein the liquid reservoir/wick portion and the atomizing element are further configured and arranged to be coupled to and separated from one another;
wherein the wick has one or more of the following characteristics: a hollow cylindrical shape or an annular shape.

2. The electronic smoking device of claim 1, wherein the wick includes a central opening in fluid communication with a central passage of the liquid reservoir/wick portion, the central passage extending away from the atomizing element and towards an air inhalation port of the electronic smoking device.

3. The electronic smoking device of claim 1, wherein the wick is attached to a base of the liquid storage volume, the base having liquid conduits configured and arranged to supply liquid to the wick.

4. The electronic smoking device of claim 2, wherein the liquid receiving side is in contact with a front face of the liquid reservoir/wick portion, the front face facing the atomizing element and configured and arranged to be permeable for liquid.

5. The electronic smoking device according to claim 4, wherein the front face encircles the central passage.

6. The electronic smoking device of claim 1, wherein the atomizing element is in direct contact with the liquid supply side.

7. The electronic smoking device of claim 1, wherein the liquid supply side has an arced shape and at least partially encompasses the atomizing element.

8. The electronic smoking device of claim 1, wherein an envelope of the atomizing element is essentially cone-shaped.

9. The electronic smoking device of claim 8, wherein the atomizing element is a heating coil with an inner wire section, around which windings with an increasing diameter are wound.

10. The electronic smoking device of claim 1, wherein the atomizing element is a heating coil, whose windings have a constant diameter.

11. The electronic smoking device of claim 1, wherein the atomizing element is a torus-shaped heating coil or comprises a spirally formed heating wire.

12. The electronic smoking device of claim 1, wherein the liquid reservoir/wick portion is configured to be replaceable.

13. A liquid reservoir/wick portion for an electronic smoking device, comprising a liquid storage volume and a wick, wherein the wick comprises a liquid receiving side that faces the liquid storage volume, and a liquid supply side opposite of the liquid receiving side, the liquid supply side facing away from the liquid storage volume; and
wherein the liquid reservoir/wick portion is configured and arranged to be detachably connected to an atomizing element within the electronic smoking device.

14. The liquid reservoir/wick portion of claim 13, wherein the wick has one or more of the following characteristics: a hollow cylindrical shape or an annular shape.

15. The liquid reservoir/wick portion of claim 13, wherein the wick is attached to a base of the liquid storage volume, the base including liquid conduits configured and arranged to supply liquid to the wick.

16. The liquid reservoir/wick portion of claim 13, wherein the wick has a central opening in fluid communication with a central passage of the liquid reservoir/wick portion, the central passage extending away from an atomizing element.

17. The liquid reservoir/wick portion of claim 13, wherein the liquid storage volume is configured and arranged to store a liquid, and the wick is configured and arranged for supplying the liquid from the liquid storage volume to an atomizing element of the electronic smoking device.

* * * * *